US006436449B2

(12) United States Patent
Gidlund

(10) Patent No.: US 6,436,449 B2
(45) Date of Patent: Aug. 20, 2002

(54) USE OF A COMPOSITION

(76) Inventor: Bo Gidlund, Marmorvägen 11 D, S-752 44 Uppsala (SE)

( * ) Notice: Subject to any disclaimer, the term of this patent is extended or adjusted under 35 U.S.C. 154(b) by 0 days.

(21) Appl. No.: 09/796,746

(22) Filed: Mar. 2, 2001

Related U.S. Application Data

(60) Provisional application No. 60/186,356, filed on Mar. 2, 2000.

(51) Int. Cl.$^7$ ................................................ A61K 35/78
(52) U.S. Cl. ........................ 424/752; 424/725; 424/773; 424/774; 424/775; 424/777; 424/94.1; 514/474
(58) Field of Search ................................ 424/725, 752, 424/773, 774, 775, 777, 94.1; 514/474

(56) References Cited

U.S. PATENT DOCUMENTS

| 4,543,212 A | 9/1985 | Heinicke |
| 5,064,858 A | 11/1991 | Sapse |
| 5,288,491 A | 2/1994 | Moniz et al. |
| 5,840,723 A | 11/1998 | Sands |

FOREIGN PATENT DOCUMENTS

| WO | WO 98/35658 A2 | 8/1998 |

OTHER PUBLICATIONS

Oscar Levand, Part 1. Some Chemical Constituents of Morinda Citrifolia L. (Noni), Thesis submitted to Graduate School of University of Hawaii, Jan. 1963.

O. A. Bushnell, et al., "The Antibacterial Properties of Some Plants Found in Hawaii", Pacific Science, vol. IV, pp. 167–183, Jul. 1950.

Alexandra Dittmar, "*Morinda citrifolia* L.–Use in Indigenous Samoan Medicine", Journal of Herbs, Spices & Medicinal Plants, vol. 1, No. 3, pp. 77–92, 1993.

Chafique Younos, et al., "Analgesic and Behavioural Effects of *Morinda citrifolia*", Planta Med., vol. 56, pp. 430–434, 1990.

Krupp M.A. and Chatton M.J., Current Medical Diagnosis and Treatment, 16$^{th}$ Annual Revision, p. 95, 1977.

Samuelsson G., Drugs of Natural Origin, A Textbook of Pharmacognosy, Swedish Pharmaceutical Press, pp. 47–51, and 294, 1999.

Anne Hirazumi, Antitumor Studies of a Traditional Hawaiian Mediciani Plant, *Morinda Itrifolia* (NONI), in Vitro and in Vivo, Dissertation submitted University of Hawaii for PhD in Biomedical Sciences (Pharmacology), Dec. 1997.

*Primary Examiner*—Francisco Prats
*Assistant Examiner*—Susan D. Coe
(74) *Attorney, Agent, or Firm*—Browdy and Neimark, P.L.L.C.

(57) ABSTRACT

Use of an extract derived from the fruits, leaves, the bark or the roots of *Morinda citrifolia* L. for the manufacture of a medicament for the treatment of a mammal suffering from tinnitus. The extract may be a liquid present in the medicament in an amount such as to give a daily dosage of 0.1–2 ml, or 0.2–1 ml, e.g. 0.4–0.7 ml, per kg body weight of the patient. The extract also may be a solid present in the medicament in an amount such as to give a daily dosage of 5–200 mg, or 10–100 mg, e.g. 20–70 mg, per kg body weight of the patient. Optionally, the medicament also may comprise lycopene, vitamine C, coenzyme Q10 and an extract from the leaves of Ginkgo biloba. The medicament may be given e.g. by oral, rectal, transdermal or inhalation administration.

18 Claims, No Drawings

USE OF A COMPOSITION

This application claims priority from provisional application No. 60/186,356, filed Mar. 2, 2000.

TECHNICAL FIELD

The present invention relates to the manufacture of a medicament for the treatment of a mammal suffering from tinnitus.

More specifically the present invention relates to the use of a composition comprising an extract from *Morinda citrifolia* L. (Rubiaceae) for the manufacture of such a medicament.

BACKGROUND ART

*Morinda citrifolia* L. (Rubiaceae), the Indian mulberry, also called noni, is an evergreen shrub tree which is native to Asia, Australia and some Pacific Islands. Its botanical description is given e.g. in Levand O. (Part I Some chemical constituents of *Morinda citrifolia* L (noni), thesis, University of Hawaii, 1963). The roots, bark, stem, leaves and fruits thereof have traditionally been used in medicine, in food and as a dye in different cultures, e.g. on Hawaii and in the French Polynesia. As an example, a plurality of indications of use is reported in the indigenous Samoan medicine, (Dittmar A."*Morinda citrifolia* L.—Use in Indigenous Samoan Medicine", J. of Herbs, Spices & Medicinal Plants, Vol. 1(3) pp 77–91 (1993)), covering a wide range of ailments, such as tooth ache (roots), septicemia (leaf), diarrhea of infants (bark) and eye complaints (fruit) . . . just to mention a few.

In view of the multiple traditional uses and alleged beneficial properties on human health of the plant, scientific studies have been undertaken to try to identify the active principles in the different parts of the plant and to verify the medicinal effects obtained.

Thus, in view of a work by Bushnell et al. (Pacific Sci. 4, 167–83 (1950)) showing the antibacterial activity of the fruit of *Morinda citrifolia* (noni fruit), Levand (supra) tried to identify the chemical constituent of the fruit which would be responsible for this activity. A hypothesis was emitted that asperuloside, an aucubin-type glucoside found in an extract from the fruit, might have some antibacterial properties. Younos C. et al. ("Analgesic and Behavioural Effects of *Morinda citrifolia*", Planta Med. 56 pp.430–434 (1990)) investigated lyophilised aqueous extracts of roots of *Morinda citrifolia* for analgesic and behavioural effects in mice, finding a dose-related central analgesic activity as well as sedative properties at doses of 500–800 mg of dried plant material/kg of body weight.

Hirazumi A. et al. (Proc. West. Pharmacol. Soc. 37: 145–146 (1994)) studied the antitumour activity of juice extracted from noni fruits on intraperitoneally implanted Lewis lung carcinoma in syngenic mice, and found that the noni juice at a dose of 15 mg per mouse significantly increased the life span of the animals. The active substance was isolated by ethanol precipitation, but was not chemically identified.

In her thesis, Hirazumi further identified the antitumour active substance as a polysaccharide-rich substance. Appendix A of the thesis gives a list of the medicinal uses of the noni plant in traditional medicine in different regions of the world, and Appendix B gives a list of chemical constituents of the different parts of the noni tree. From Appendix B it can be seen that each part of the plant contains a varying number of different chemical constituents; in the fruits 66 different compounds are reported to have been found.

In an article intitulated "The pharmacologically active ingredient of noni" Heinicke, R. M. states that the active ingredient of the noni fruit in fact is not present in any substantial amount in the fruit itself, but is generated, on ingestion of the fruit or of an extract thereof, within the human body from a precursor present in the fruit. The active substance is said to be an alkaloid, which the author names xeronine, its precursor being named proxeronine. The author further emits some hypotheses on the biochemistry involved in the generation of the alkaloid from its precursor as well as on the mode of action of the alkaloid within the body, and finally recommends a daily intake of 100 ml of noni juice half an hour before breakfast. The physical conditions that might be favourably influenced are said to be e.g. high blood pressure, menstrual cramps, arthritis, gastric ulcers, sprains, injuries, mental depression, senility, poor digestion, atherosclerosis, blood vessel problems, drug addiction, pain etc.

U.S. Pat. No. 4,543,212 (1985) to Heinicke relates to xeronine as a new alkaloid, and describes its characterization, assay, mode of action and utility within the medical, food and industrial fields. A process for obtaining xeronine from plant, bacteria and animal alkaloid producing lipophilic extracts is given. The activity of xeronine is stated to be due to its capacity to adhere to specific proteins as a modifier of rigidity of the same. The author notes that samples of xeronine acted as excellent anti-inflammatory agents when injected into mice, inhibited the in vitro aggregation of blood platelets by adenosine diphosphate, caused the debridement of burn eschars on mice, stimulated the partial breakdown of wheat grits and caused the aggregation of casein. Moreover, prediction is made that xeronine would be an effective antidote against alkaloid poisoning and addiction, and could be applied for the alleviation of symptoms of one type of senility and as a general stimulant or tonic. Finally, xeronine is also said to act as a coregulator for many hormone actions, a lack thereof thus being a possible cause contributing to e.g. diabetes.

U.S. Pat. No. 5,288,491 (1994) to Moniz relates to the noni plant as a medicinal product and teaches a method of processing the fruit into powder, mainly by picking, washing, cleaning and mashing the fruit, and then drying the pulp by thermal treatment in several steps and finally crushing and grinding the dried wafers. The author refers to the paper by Heinicke and proposes that either pure xeronine or a system that releases xeronine be produced.

From the above, it appears that *Morinda citrifolia* L. has been used and recommended for use against an important number of diseases and ailments, and that a theory exists that an important active ingredient of at least the fruits of the plant is xeronine, which possibly may be present therein only in the form of its precursor.

Tinnitus is the perception of sound when no external sound is present; it is often referred to as "ringing in the ears." It can also take the form of hissing, roaring, whistling, chirping or clicking. The sensation may be objective (heard by the examiner) or subjective.

Objective tinnitus is uncommon and is caused by transmitted vascular vibrations in the blood vessels of the head and neck or by rythmic rapid contractions of the muscles of the soft palate or middle ear (Current medical diagnosis and treatment, 16th Annual revision, by Krupp M. A. and Chatton M. J. p.95 (1977)).

Subjective tinnitus is much less well understood. Although its etiology is at present not known, it is presumed to be due to irritation of nerve endings in the cochlea by degenerative vascular or vasomotor disease. It usually accompanies hearing loss or other disorders. The most frequent cause of tinnitus seems to be exposure to loud noise, either over an extended period of time or as one extreme incident.

The subjective form of tinnitus is very prevalent among adults. E.g. in a survey from Great Britain, about 10% of adults reported having prolonged, spontaneous tinnitus, with 1–3% reporting tinnitus severe enough to be disabling. Severe tinnitus is disabling due to the psychological effect of "hearing" sounds or noise continuously. Tinnitus prevents concentration, disrupts or prevents sleep, and in severe cases often leads to depression.

As stated in U.S. Pat. No. 5,840,723 (Sands), different modes of treatment are proposed to alleviate tinnitus, such as masking the noise by use of background music or "white noise", relaxation training or medication. Medication has included intravenous administration of local anesthetics (lidocaine), trans-tympanic injections of local anesthetics, administration of zinc, steroids, anticonvulsants (carbamazepine), tranquilizers (alprazolam), barbiturates, antidepressants (trimipramine, nortryptyline), and calcium channel blockers (flunarizine), although in general with limited efficacy, or low acceptability due to the administration route in the case of the trans-tympanic injections. In the above cited U.S. Pat. No. 5,840,723 a treatment based on the use of quinoxaline derivates is disclosed.

Use of an extract from the leaves of Ginkgo biloba (Ginkgoaceae) as a herbal remedy for treatment of i.a. tinnitus has been proposed ("Drugs of Natural Origin, A Textbook of Pharmacognosy" by Samuelsson G., Swedish Pharmaceutical Press (1999) p.294). The leaves contain a class of diterpenes, called ginkgolides, as well as a sesquiterpene derivative, called bilobalide, and a great number of flavonoids. In the extract, the ginkgolides and the flavonoids are regarded as the pharmacologically active ingredients.

International application WO 98/35658 relates to the use of 2,3-dimethoxy-5-methyl-6-decaprenyl-1,4-benzoquinone, also referred to as coenzyme Q10, as a pharmaceutical for the treatment of a multitude of indications, amongst others tinnitus. A capsule preparation containing from 30 mg to 120 mg of coenzyme Q10 is mentioned.

U.S. Pat. No. 5,064,858 relates to a composition for the treatment of individuals addicted to narcotics or individuals having age-related conditions such as tinnitus and Alzheimer's disease. The composition contains a protected complex of procaine and a complexing agent for procaine. Among a number of other additional compounds optionally present in the preparation, mention is made of zinc citrate and ascorbic acid, the former as a buffer and the latter as a preferred complexing agent. Moreover, it is stated that a positive synergistic effect is believed to be obtained by the combination of procaine, ascorbic acid and zinc citrate as compared to the use of another selection of buffer and complexing agent.

SUMMARY OF THE INVENTION

The present invention is based on the discovery that an extract from *Morinda citrifolia* L. when administered to a person suffering from tinnitus will give a substantial relief of the ailment.

The present invention thus relates to the use of an extract from *Morinda citrifolia* L. for the manufacture of a medicament for the treatment of a mammal suffering from tinnitus, as well as to a method of treating a mammal suffering from tinnitus.

The extract may be derived from the fruits, the roots, the leaves and the bark of *Morinda citrifolia* L, and may be in a liquid or solid state.

The medicament may be in a form suitable for oral, rectal, inhalation or transdermal administration.

The medicament optionally may comprise one or more other active ingredients chosen from lycopene, an extract from the leaves of Ginkgo biloba, vitamin C and coenzyme Q10.

The combined use of two or more of the active ingredients as referred to above advantageously will give an enhanced antitinnitus effect.

DETAILED DESCRIPTION OF THE INVENTION

The extract from *Morinda citrifolia* L. may be derived from the roots, the bark, the leaves or the, fruits using extraction techniques well-known to the persons skilled in the art or described in the literature (e.g. in "Drugs of Natural Origin, A Textbook of Pharmacognosy" by Samuelsson G., Swedish Pharmaceutical Press (1999), cf. also references therein.).

The extract from the fruits may be either liquid, i.e. the juice as pressed from the fruits and treated in the way conventional to the art, or solid, i.e. dry, e.g. as a powder, e.g. as obtained by processing as described in U.S. Pat. No. 5,288,491 (1994) to Moniz.

As to the optional ingredients, lycopene, also referred to as $\psi$, $\psi$-carotene or (all trans)-lycopene, is a carotenoid of $C_{40}H_{56}$ occurring in ripe fruit, such as water melons and tomatoes. One kg of fresh ripe tomatoes may yield about 0.02–0.03 g lycopene. Carotenoids are nowadays thought to be highly efficient antioxidants. They are therefore being increasingly used e.g. in health products and in health food products to inactivate noxious free radicals generated in the human body. Also, there are studies showing that lycopene may be effective against different forms of cancers.

Due to concentrating effect of processing operations, such as cooking, where lycopene is not decomposed, the content of lycopene in processed tomato products is even higher than in the fresh tomatoes. Thus, the content of lycopene in 100 grams tomato ketchup amounts to around 10 mg, whereas the content of lycopene of the same amount of tomato juice is somewhat lower, around 9 mg, the content of lycopene of 100 grams of dried tomatoes being approximately the same, viz. around 9 mg.

Lycopene may also be synthesised by chemical or biosynthetic methods, or provided as a pure extract from a fruit or vegetable source, such as tomatoes. E.g. in U.S. Pat. No. 5,871,574 to Kawaragi et al. a process is provided for collecting tomato pigment.

In U.S. Pat. No. 5,962,756 to Koch et al. a process is provided for preparing natural carotenoid concentrates from plant material.

On the other hand, in U.S. Pat. No. 5,965,183 to Hartal et al. a process is provided for the preparation of stable lycopene concentrates.

For the purpose of the present invention, lycopene may be included either in the form of a processed tomato product, such as tomato ketchup, tomato juice, dried tomato powder etc, or as a pure extract or synthetic product, or as a combination thereof. However, when lycopene is included in the form of a processed tomato product, such as tomato ketchup, this will result in a further advantageous effect of improving the general taste of the medicament.

When lycopene is present in the medicament of the invention, a suitable amount thereof will be one providing a daily dosage of 0.1 to 30 mg, or 0.2 to 15 mg, e.g. 0.5–5 mg, per kg body weight of the patient.

The extract from the leaves of Ginkgo biloba may be obtained by conventional extraction techniques, e.g. as described in Samuelsson G. (supra) pp 47 and references therein.

The further optional active ingredients, coenzyme Q10 and vitamin C, are commercially available or may be obtained by conventional synthesis or extraction methods known to the person skilled in the art.

The liquid extract from *Morinda citrifolia* will be present in the medicament in an amount such as to provide a daily dosage of 0.1–2 ml, or 0.2–1 ml, e.g. 0.4–0.7 ml, per kg body weight of the patient.

The dry extract from *Morinda citrifolia* will be present in the medicament in an amount such as to provide a daily dosage of 5–200 mg, or 10–100 mg, e.g. 20–70 mg, per kg body weight of the patient.

Optionally, vitamin C will be present in the medicament in an amount such as to provide a daily dosage of 0.05–20 mg, or 0.1–10 mg, e.g. 1–5 mg, per kg body weight of the patient.

Optionally, coenzyme Q10 will be present in the medicament in an amount such as to provide a daily dosage of 0.01–3 mg, or 0.1–1 mg, e.g. 0.2–0.5 mg, per kg body weight of the patient.

Optionally, the extract from the leaves of Ginkgo biloba will be present in the medicament in an amount such as to provide a daily dosage of 0.5–10 mg, or 1–7 mg, e.g. 2–5 mg, per kg body weight of the patient.

As an example, a daily dosage of a medicament comprising 10–100 ml of a liquid extract from *Morinda citrifolia* L., or 0.5–10 g of a dry extract from *Morinda citrifolia* L., and optionally 5–500 mg of vitamin C, and/or 1–150 mg of coenzyme Q10 and/or 10–500 mg of an extract from the leaves of Ginkgo biloba may be administered, as one single dose or subdivided into multiple doses.

The daily dosage will also depend on factors such as age, general state of health, severity of the tinnitus, other medication etc. It will also be appreciated that it in some cases may be sufficient to manage with less than the previously mentioned minimum amount, whereas the said upper limit in other cases may have to be exceeded.

Having regard to the particular mode of administration, the medicament of the invention, besides the active ingredient(s), may also incorporate any suitable additive, adjuvant and excipient as conventionally used within the pharmaceutical field, provided these do not unduly interfere with the active ingredients.

The medicament in a form suitable for oral administration may be e.g. a liquid solution, emulsion or suspension, granules, a pill, a capsule, a tablet etc, to be administered in a single daily dose or as several daily doses. Additionally, the medicament may contain a solvent, a filler, a flavouring agent, a disintegrant, a preservative, a colouring agent etc as known to the persons skilled in the art.

Furthermore, the medicament for oral administration may be a sustained release preparation such as a depot tablet or capsule.

The medicament in a form suitable for rectal administration may be a suppository incorporating any suitable formulating aid, suppository base, a glidant etc, as known to the persons skilled in the art.

For transdermal administration the medicament of the invention may be incorporated into a plaster, using methods and materials well known to the persons skilled in the art.

For the inhalation administration, the medicament of the invention may be formulated into an aerosol preparation.

It will be understood that the administration forms mentioned above are only examples, and that other modes of administration may also be contemplated by the person skilled in the art without departing from the scope of the invention.

The medicament of the invention is prepared by processing of a composition of active ingredient(s) and any suitable excipients, in a conventional manner corresponding to the selected administration form, as known to the persons skilled in the art or as described e.g. in the European Patent Application 0 208 235.

EXAMPLE

A male patient, aged 87, who for several years had been suffering from a severe tinnitus, was given a liquid extract from the fruit of *Morinda citrifolia* at a daily dosage of 30 ml, corresponding to a daily dosage per kg body weight of 0.4 ml.

At the start of the treatment period, the patient experienced a constant whistling and roaring noise in the ears.

After 14 days of treatment, the patient experienced that a reduction of the noise in the ears was taking place.

After 1 month of treatment, the patient estimated that the noise was very disturbing during 75% of the time of the day, and less disturbing during the remaining 25% of the time of the day. Moreover, the patient estimated that the maximum intensity of the noise had been reduced to 65–75% of its initial maximum value.

After 2 months, the period of time during which the patient experienced less disturbance from the noise had increased to 50% of the day.

After 3 months, the patient now estimated that the noise was disturbing during 25% of the time of the day, and less disturbing during the remaining 75% of the time of the day, and that the maximum intensity of the noise had been substantially reduced.

After 5 months of treatment, the noise was experienced as disturbing only occasionally, i.e. once or twice a month.

After 8 month of treatment, the patient experienced only intermittently a very faint sound in the ears.

What is claimed is:

1. A method of treating tinnitus in a mammal comprising administering to a mammal in need of such treatment a therapeutically effective amount of an extract derived from the fruits, the leaves, the bark or the roots of *Morinda citrifolia* L.

2. A method according to claim 1, wherein the extract is administered in the form of a medicament composition which further comprises at least one additional active ingredient selected from the group consisting of lycopene, vitamin C, coenzyme Q10 and an extract from the leaves of Ginkgo biloba.

3. The method according to claim 1, wherein said extract is in liquid form.

4. The method according to claim 1 wherein said therapeutically effective amount is at a daily dosage of 0.1–2 ml per Kg body weight of said mammal, and said mammal is a human patient.

5. The method of claim 4, wherein said daily dosage is 0.4–0.7 ml per Kg body weight of said patient.

6. The method of claim 1 wherein said extract is in solid form.

7. The method according to claim 6 wherein said therapeutically effective amount is at a daily dosage of 5–200 mg per Kg body weight of said mammal, and said mammal is a human patient.

8. The method of claim 7, wherein said daily dosage is 20–70 mg per Kg body weight of said patient.

9. The method of claim 1 wherein said extract is in a form suitable for oral, rectal, inhalation, or transdermal administration, and is administered orally, rectally, by inhalation or transdermally.

10. The method of claim 2 wherein lycopene is present in said medicament composition and is administered in an amount to give a daily dosage of lycopene of 0.1–30 mg per Kg body weight of the mammal, and the mammal is a human patient.

11. The method of claim 10 wherein said amount of lycopene is 0.5–5 mg per Kg body weight of said patient.

12. The method of claim 2 wherein vitamin C is present in said medicament composition and is administered in an amount to give a daily dosage of vitamin C of 0.05–10 mg per Kg body weight of the mammal, and the mammal is a human patient.

13. The method of claim 12 wherein said amount of vitamin C is 1–3 mg per Kg body weight of said patient.

14. The method of claim 2 wherein coenzyme Q10 is present in said medicament composition and is administered in an amount to give a daily dosage of coenzyme Q10 of 0.01–3 mg per Kg body weight of the mammal, and the mammal is a human patient.

15. The method of claim 14 wherein said amount of coenzyme Q10 is 0.2–0.5 mg per Kg body weight of said patient.

16. The method of claim 2 wherein extract from the leaves of Ginkgo biloba is present in said medicament composition and is administered in an amount to give a daily dosage of extract from the leaves of Ginkgo biloba of 0.2–10 mg per Kg body weight of the mammal, and the mammal is a human patient.

17. The method of claim 16 wherein said amount of extract from the leaves of Ginkgo biloba is 2–5 mg per Kg body weight of said patient.

18. The method of claim 2 wherein said medicament composition contains two of said additional active ingredients, three of said additional active ingredients, or all four of said additional active ingredients.

* * * * *